(12) United States Patent
Ahlmén et al.

(10) Patent No.: US 8,978,652 B2
(45) Date of Patent: Mar. 17, 2015

(54) ANESTHETIC BREATHING APPARATUS HAVING IMPROVED MONITORING OF ANESTHETIC AGENT

(75) Inventors: Christer Ahlmén, Sollentuna (SE); Marlo Loncar, Ekerö (SE)

(73) Assignee: Maquet Critical Care AB, Solna (SE)

( * ) Notice: Subject to any disclaimer, the term of this patent is extended or adjusted under 35 U.S.C. 154(b) by 909 days.

(21) Appl. No.: 12/742,757

(22) PCT Filed: Nov. 14, 2007

(86) PCT No.: PCT/EP2007/062357
§ 371 (c)(1),
(2), (4) Date: Sep. 21, 2010

(87) PCT Pub. No.: WO2009/062550
PCT Pub. Date: May 22, 2009

(65) Prior Publication Data
US 2011/0017211 A1    Jan. 27, 2011

(51) Int. Cl.
*A61M 16/01* (2006.01)
*A61M 16/00* (2006.01)
*A61M 16/10* (2006.01)

(52) U.S. Cl.
CPC ............. *A61M 16/01* (2013.01); *A61M 16/104* (2013.01); *A61M 2205/17* (2013.01); *A61M 2230/437* (2013.01)
USPC ............. 128/204.22; 128/204.18; 128/204.21; 128/203.25

(58) Field of Classification Search
CPC ............. A61M 16/01; A61M 16/104; A61M 16/1035; A61M 2230/437; A61M 2016/1035; G01N 33/007
USPC ............. 128/203.14, 203.12, 203.25, 204.18, 128/204.21, 204.22, 204.23, 205.11
See application file for complete search history.

(56) References Cited

U.S. PATENT DOCUMENTS 4,905,685 A * 3/1990 Olsson et al. ............. 128/203.12
5,237,990 A * 8/1993 Psaros et al. ............. 128/204.21
(Continued)

FOREIGN PATENT DOCUMENTS

WO    WO 2007/033271         3/2007
WO    WO 2007033271 A1 *     3/2007
(Continued)

*Primary Examiner* — Justine Yu
*Assistant Examiner* — Douglas Sul
(74) *Attorney, Agent, or Firm* — Schiff Hardin LLP

(57) ABSTRACT

An anesthetic breathing apparatus has a first gas analyzer arranged to provide gas measurement data related to a first sample point to a control unit that is arranged in a servo or feedback control system configured to adjust delivery of a vaporized anesthetic agent from an anesthetic vaporizer to a delivery point in an inspiratory branch of a breathing circuit of the anesthetic breathing apparatus, The first sampling point is arranged in the breathing circuit downstream and close to the delivery point. A second gas analyzer arranged to be operated in a first mode of operation to provide gas measurement data for patient monitoring, and arranged to be operated in a second mode of operation to provide gas measurement data to the control unit. A switch over unit is fluidly connected to the second gas analyzer, and arranged to switch fluid communication of said second gas analyzer between the first sample point for the second mode of operation and a second sample point for the first mode of operation. The second sample point is arranged in a patient tubing close to a Y-piece at a patient connected to the breathing circuit.

23 Claims, 3 Drawing Sheets

(56) References Cited

U.S. PATENT DOCUMENTS

| | | | | |
|---|---|---|---|---|
| 5,694,924 A | * | 12/1997 | Cewers | 128/204.21 |
| 5,806,513 A | * | 9/1998 | Tham et al. | 128/204.22 |
| 6,691,705 B2 | * | 2/2004 | Dittmann et al. | 128/203.25 |
| 7,290,544 B1 | * | 11/2007 | Sarela et al. | 128/202.22 |
| 7,703,455 B2 | * | 4/2010 | Bunke et al. | 128/204.14 |
| 8,127,762 B2 | * | 3/2012 | Loncar et al. | 128/203.12 |
| 2002/0014236 A1 | | 2/2002 | Dittmann et al. | |
| 2002/0111747 A1 | * | 8/2002 | Nishina et al. | 702/24 |
| 2005/0103338 A1 | | 5/2005 | Bunke et al. | |
| 2006/0207593 A1 | * | 9/2006 | Dittmann et al. | 128/203.12 |

FOREIGN PATENT DOCUMENTS

| | | |
|---|---|---|
| WO | WO 2007/071756 | 6/2007 |
| WO | WO 2007071756 A1 * | 6/2007 |

* cited by examiner

ANESTHETIC BREATHING APPARATUS HAVING IMPROVED MONITORING OF ANESTHETIC AGENT

BACKGROUND OF THE INVENTION

1. Field of the Invention

This invention pertains in general to the field of anesthetic breathing apparatuses. More particularly the invention relates anesthetic breathing apparatuses having improved monitoring of anesthetic agents.

2. Description of the Prior Art

Anesthetic breathing apparatus are known. For instance in WO2007/071756 of the same applicant as the present application, various set-ups of anesthetic breathing apparatus are disclosed. An anesthetic gas monitor is normally provided for monitoring a concentration of an anesthetic agent delivered to a patient from the anesthetic breathing apparatus.

Anesthetic breathing apparatuses, such as disclosed in WO2007/071756, conventionally comprise a single gas monitor providing, amongst others, a concentration of anesthetic agents and other gas components, usually in a breathing circle of the anesthetic breathing apparatus. The monitored concentration is conventionally a parameter presented to the operator of the anesthetic breathing apparatus for controlling and perhaps managing adjustments of anesthesia performed by means of the anesthetic breathing apparatus.

It might be an issue causing deteriorated operation of the anesthesia when the single gas monitor is not working properly. For instance, when the gas monitor is out of calibration, the patient might be provided with unintended high or low concentrations of an anesthetic agent due to erroneous adjustments of the anesthetic breathing apparatus.

An anesthetic breathing apparatus having a single anesthetic gas monitor with improved safety is disclosed in EP1140264A1 of GE Healthcare. A feedback control system is provided, which periodically compares a measuring value obtained from a fresh gas sample with a real reference value of the sample, based on which required safety measures are taken. This means both that a calibration is done at defined time intervals and that a real and known reference value has to be present in the system. At least the latter is difficult to provide in practice as a reference value may also be erroneous.

Also, when having fast responsive anesthetic vaporizers of the injector type, these need to be controlled by a feedback loop that is based on a real time measurement of delivered anesthetic agent concentration. In case the measurement of the concentration of the anesthetic agent fails in this control loop, erroneous concentrations may be delivered by the anesthetic vaporizer.

An anesthetic breathing apparatus having two anesthetic gas monitors is disclosed in US2005/0103338A1 of Dräger Medical AG. A first gas monitor is connected to the trailing side of a mixing chamber volume in a ring line and a second gas monitor is connected to a patient connection. A plausibility comparison between the measured values of the first gas monitor and the second gas monitor is made.

However, the system does not take into consideration that the actual concentrations at the two different measurement points of the two different anesthetic gas monitors may be different. Also, the system may shut down delivery of anesthetic agent of the patient during surgery even if the concentration of anesthetic agent delivered to the patient is correct, e.g. in case a sample line of one of the two anesthetic gas monitors is clogged and thus measurement values are wrong.

Hence, an improved anesthetic breathing apparatus would be advantageous and in particular allowing for increased operational safety and/or patient safety would be advantageous.

SUMMARY OF THE INVENTION

Accordingly, embodiments of the present invention preferably seeks to mitigate, alleviate or eliminate one or more deficiencies, disadvantages or issues in the art, such as those discussed above, singly or in any combination by providing an anesthetic breathing apparatus, a method, and a computer-readable storage medium.

According to one aspect of the invention, an anesthetic breathing apparatus is provided. The anesthetic breathing apparatus has a first gas analyzer arranged to provide gas measurement data related to a first sample point to a control unit that is arranged in a feedback control system configured to adjust delivery of a vaporized anesthetic agent from an anesthetic vaporizer to a delivery point in an inspiratory branch of a breathing circuit of the anesthetic breathing apparatus. The first sampling point is arranged in the breathing circuit downstream and close to the delivery point. A second gas analyzer is arranged to be operated in a first mode of operation to provide gas measurement data for patient monitoring, and is arranged to be operated in a second mode of operation to provide gas measurement data to the control unit. The second gas analyzer is arranged to sample at a second sample point arranged close to a patient connection for the first mode of operation and at the first sampling point in the second mode of operation.

According to yet another aspect of the invention, a method is provided. The method is a method of improving monitoring of anesthetic agents in an anesthetic breathing apparatus. The method includes providing gas measurement data related to a first sample point from a first gas analyzer to a control unit, and adjusting delivery of a vaporized anesthetic agent from an anesthetic vaporizer to a delivery point in an inspiratory branch of a breathing circuit of the anesthetic breathing apparatus by the control unit in a feedback control system. The first sampling point is arranged in the breathing circuit downstream and close to the delivery point. The method further includes providing gas measurement data from a second gas analyzer in a first mode of operation for patient monitoring, and in a second mode of operation providing gas measurement data to the control unit. The method further includes switching fluid communication of the second gas analyzer between the first sample point for the second mode of operation and a second sample point for the first mode of operation by controlling a switch over unit fluidly connected to the second gas analyzer the first and second sample point, wherein the second sample point is arranged close to a patient connection a patient connected to the breathing circuit.

According to a further aspect of the invention, a computer-readable storage medium encoded with programming instructions is provided for improving monitoring of anesthetic agents in an anesthetic breathing apparatus. The programming instructions are processed by a computer and include a first code segment for providing gas measurement data related to a first sample point from a first gas analyzer to a control unit, and adjusting delivery of a vaporized anesthetic agent from an anesthetic vaporizer to a delivery point in an inspiratory branch of a breathing circuit of the anesthetic breathing apparatus by the control unit in a servo feedback control system, wherein the first sampling point is arranged in the breathing circuit downstream and close to the delivery point. The programming instructions include a second code segment for providing gas measurement data from a second gas analyzer in a first mode of operation for patient monitoring, and in a second mode of operation to provide gas measurement data to the control unit. The programming instructions include a third code segment for switching fluid communication of the second gas analyzer between the first sample point for the second mode of operation and a second sample point for the first mode of operation by controlling a switch over unit fluidly connected to the second gas analyzer the first and second sample point, wherein the second sample point is arranged in a patient tubing close to a patient connected to the breathing circuit.

DESCRIPTION OF THE PREFERRED EMBODIMENTS

Figure 1:
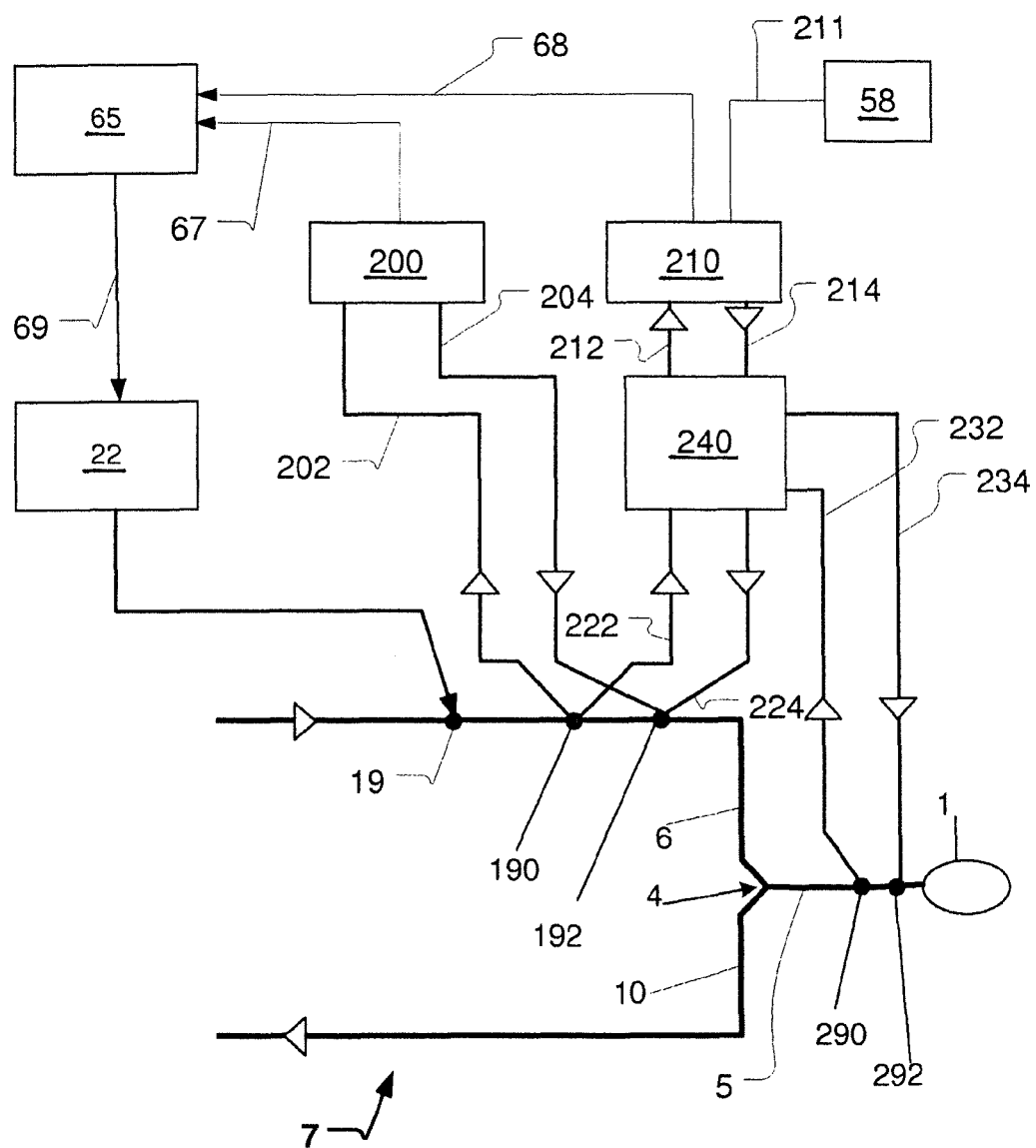
FIG. 1 is a schematic drawing illustrating an embodiment of the invention.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to anesthesia machines or anesthesia systems. However, it will be appreciated that the invention is not limited to this application but may be applied to many other anesthetic breathing apparatus, including for example an intensive care ventilator with added anesthetic breathing circle and anesthetic vaporizers.

An anesthesia system is generally devised to deliver anesthesia gas and oxygen gas to a patient according to operator set concentrations. In a conventional anesthesia circle (re-breathing) system the operator controls the amount of fresh gas delivered to the circle system through the fresh gas setting, normally a knob on the panel. Higher settings means faster change of gas concentrations, when the changes in concentrations are made. High settings also guarantee that the patient receives a large enough amount of the life sustaining oxygen gas. A drawback thereof is that high fresh gas setting also means high cost for the anesthesia gas.

In an anesthetic breathing apparatus, a servo or feedback control system based on a gas analyzer continuously during the inspiration regulates the amount of anesthetic agent delivered to the patient, while the amount of fresh gas is kept at a suitable low value that still is enough for keeping the gas concentrations at set values.

The gas analyzer may also provide measurement data for other gaseous components, such as Oxygen, Nitric Oxide, Carbon Dioxide, and perhaps further gases, such as Nitric Oxide, Xenon, etc. One or more such gas analyzer may be present in anesthetic breathing apparatuses. For instance, one gas analyzer may be dedicated to the servo control feedback and another gas analyzer may be provided for patient monitoring.

The anesthetic agent is delivered into the anesthetic breathing apparatus by means of an anesthetic agent delivery device. The anesthetic agent delivery device may be implemented in the form of an anesthetic vaporizer arranged to vaporize a liquid volatile anesthetic into a flow of gas that is transported for delivery to the patient in a breathing circuit 7. Examples for volatile anesthetic agents include agents known as Halothane, Isoflurane, Sevoflurane, Enflurane, or Desflurane.

Figure 2:
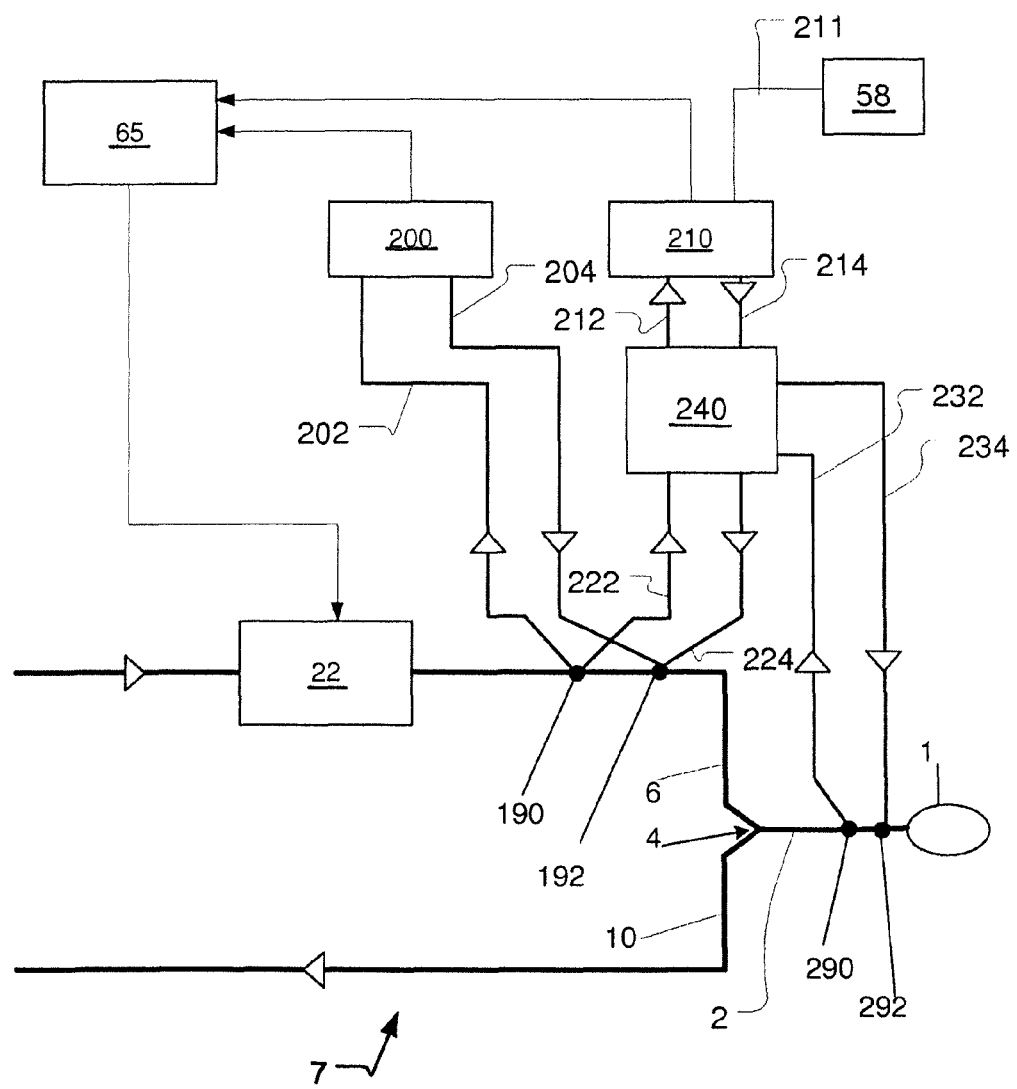
FIG. 2 is a schematic drawing illustrating another embodiment of the invention.
Figure 3:
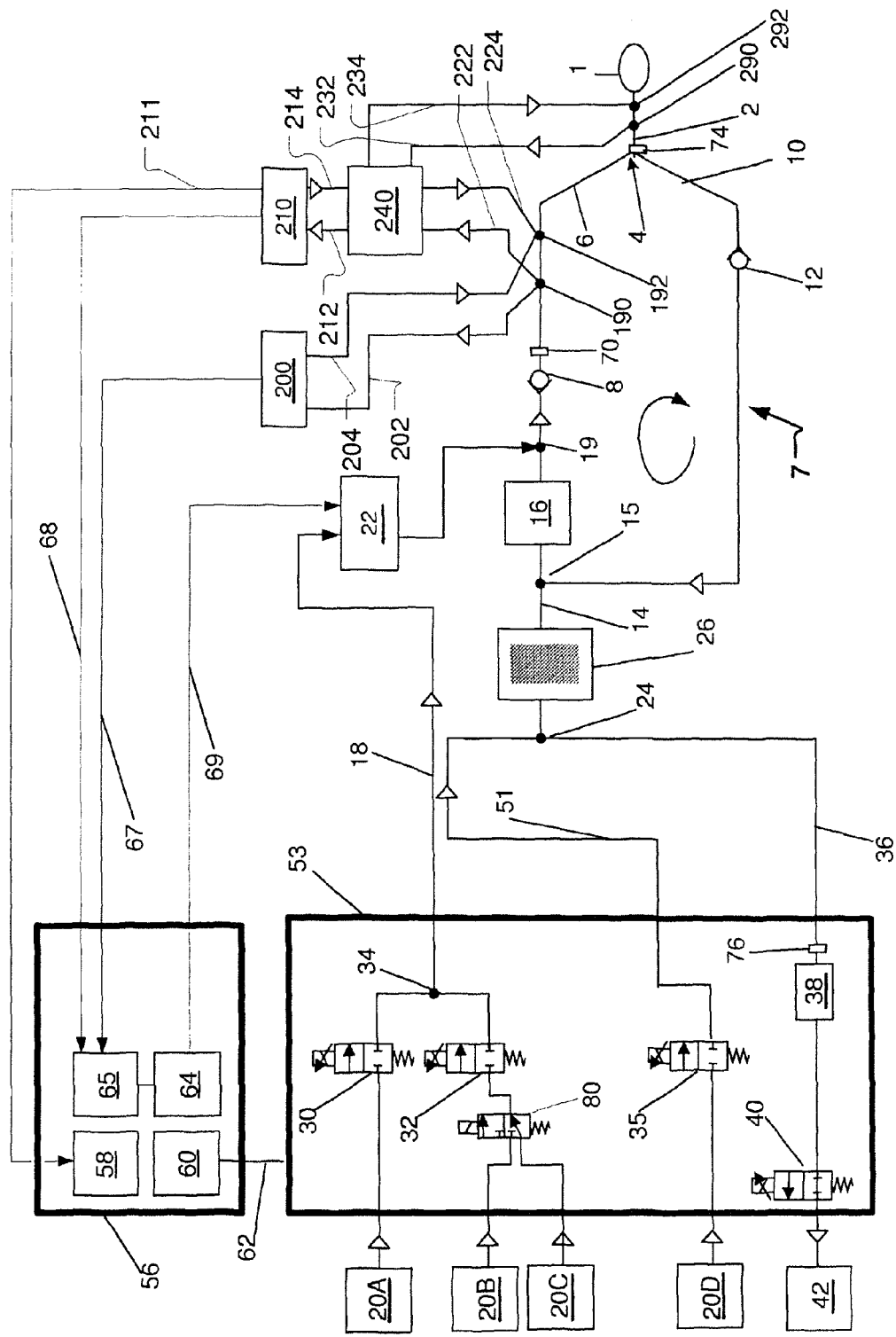
FIG. 3 is a schematic drawing illustrating an exemplary anesthetic breathing apparatus comprising an embodiment of the invention.

In some embodiments the anesthetic agent delivery device may be implemented as a delivery device of gaseous anesthetic agents, such as Xenon. Delivery of anesthetic agents by means of the anesthetic agent delivery device may be done directly into a breathing circuit, e.g. by injection methods, such as illustrated in FIG. 2, or alternatively it may be delivered via a suitable tubing to the breathing circuit, e.g. via junction 19, such as shown in FIG. 1 and FIG. 3.

In case only a single gas analyzer was available for this servo or feedback control system, and the single gas analyzer fails in measuring the gas concentration correctly, the delivered gas concentration would deviate from the set value. In order to detect that failure and both alert the personal and prohibit the machine from delivering too high anesthesia gas concentrations, a second gas analyzer is provided in embodiments of the present invention. The second gas analyzer is used for redundantly measuring the gas concentrations, at least when a deviation is detected.

When redundantly measuring the gas concentrations, sampling and return of the measured gas is done from and to the same point in the breathing circuit as is done for the servo control loop feedback gas analyzer in order to be sure that the same gas is measured and that this is done under the same conditions.

In case the measured gas concentration values provided by the first gas analyzer differ from the measured gas concentration values provided by the second gas analyzer more than, e.g. from a patient safety point of view, a specified value, an alarm may be generated to alert the personal and at the same time the vaporizer that delivers the anesthetic agent may be automatically shut down.

In order to use the second gas analyzer for ordinary patient monitoring, e.g. for providing data for visually showing curves and measured inspiratory and expiratory gas parameters on a screen, the second gas analyzer may alternate between sampling gas inside the anesthetic breathing apparatus, close to the point where the anesthetic vaporizer provides vaporized anesthetic agent in the breathing circuit and where the first gas analyzer samples gas, and sampling gas at the y-piece close to the patient.

By normally sampling at the y-piece and in case a too low concentration value is measured the sampling point is switched by a pneumatic switch to the internal sampling point. In this way an occlusion of the sampling line connected to the y-piece close to the patient may be detected and the vaporizer must not be switched off since the measurement of anesthetic agent concentration may now be correctly done via an unclogged line, close to the vaporizer.

In FIG. 1 a portion of an anesthetic breathing apparatus is illustrated including an embodiment of the present invention. A first gas analyzer 200 provides gas measurement data via a line 67 to a control unit 65. A second gas analyzer 210 provides gas measurement data via a line 68 to the control unit 65. The control unit 65 is part of a servo or feedback control system, using the gas measurement data from the first gas analyzer provided via line 67 as a feedback signal via a control line 69 for adjusting delivery of an anesthetic agent from an anesthetic agent delivery device.

In the embodiment described with reference to FIG. 1, a vaporized anesthetic agent is delivered from an anesthetic vaporizer 22. In the present embodiment, the vaporizer 22 is positioned outside of a patient breathing circle 7 of the anesthetic breathing apparatus.

The vaporizer 22 is in this embodiment arranged to deliver the vaporized anesthetic agent via a line in communication with the breathing circuit at a junction 19. During the inspiratory phase, the anesthetic agent is, downstream of junction 19, blended with gas arriving upstream from the junction 19 in the inspiratory tubing 6 of the breathing circle 7 towards a Y-piece 4 and further into a patient 1. Inhalation gas arriving upstream from the junction 19 may in itself comprise a certain concentration of anesthetic agent, e.g. previously exhaled by the patient and stored in a volume reflector and/or adsorber (e.g. as shown in FIG. 3). A sample of the blended gas is taken at a first sample point 190 in the breathing circuit 7. Exhaled gas is conveyed in an expiratory branch 10 of the breathing circle 7.

From the first sample point 190, a first sample line 202 leads to the first gas analyzer 200. When analyzed in the first gas analyzer 200, the sample gas is returned to the breathing circuit 7 via a sample return line 204 and via a sample return junction 192 downstream of the first sample point 190.

A second sample line 222 is fluidly connected from the first sample point 190 to a switch over unit 240. The switch over unit 240 has one or more on-off valves suitably arranged for either coupling a first set of lines 222, 224 or a second set of lines 232, 234 to a third set of lines 212, 214 with the second gas analyzer 210.

Sample gas taken from the first sample point 190 may be returned to the breathing circuit 7 at the first sample return junction 192 via a second sample return line 224.

A third sample line 232 and a third sample return line 235 are fluidly connected to a patient tubing 2 close to a Y-piece 4 at patient 1, via a second sample point 290 and a second sample return point 292.

The switch over unit 240 further may fluidly connect either the second sample line 222 and the second sample return line 224 in a first mode of operation, or the third sample line 232 and the third sample return line 234 in a second mode of operation, to a fourth sample line 212 and a fourth sample return line 214, respectively. The second gas analyzer 210 may thus alternate between sampling gas inside the anesthetic breathing apparatus, close to the point where the anesthetic vaporizer provides vaporized anesthetic agent in the breathing circuit and where the first gas analyzer 200 samples gas, and sampling gas at the Y-piece, close to the patient.

The second gas analyzer 210 is thus, in the first mode of operation of switch over unit 240 arranged for redundantly measuring the gas concentrations in the breathing circuit.

Measurement data from the second gas analyzer 210 is provided to the control unit 65 via a line 68. Sampling and return of the measured gas is done from and to the same point 190, 192 in the breathing circuit 7 as is done for the servo feedback control gas analyzer in order to be sure that the same gas is measured and that this is done under the same conditions.

In case control unit 65, during the inspiration phase, upon comparison of the measured gas concentration values provided by the first gas analyzer 200 and the second gas analyzer 210, detects a difference, suitable action may be initiated. For instance when the difference exceeds an allowed measurement error threshold, or a specified difference value from a patient safety point of view, an alarm may be generated to alert the personal and at the same time the vaporizer that delivers the anesthetic agent may be automatically shut down.

One or more such gas analyzers may be present in anesthetic breathing apparatuses. For instance, one gas analyzer may be dedicated to the servo control feedback and another gas analyzer may be provided for patient monitoring.

In some embodiments the anesthetic agent delivery device may be implemented as a delivery device of gaseous anesthetic agents, such as Xenon.

As each of the first and second gas analyzers may provide measurement data for one or more anesthetic agents, and/or other gaseous components, such as Oxygen, Nitric Oxide, Carbon Dioxide, and perhaps further gases, such as Nitric Oxide, Xenon, etc., this verification of correct function may be done by basing this comparison one or more of these measurable agents and/or gases.

For instance, in some embodiments the concentration of a specific single anesthetic agent may be detected at the first sampling point 190 and at the second sampling point 290 during inspiration. In practice these two measurements should be substantially identical during normal operation of the anesthetic breathing apparatus. In case of deviations, the measurement based on redundant measurement at the same sampling point by the two independent gas analyzers may be performed to identify potential malfunctions.

In some embodiments, the concentration of a specific single gaseous component may be detected at the first sampling point 190 and at the second sampling point 290 during inspiration. The gaseous component may for instance be Oxygen or Nitrous Oxide. In practice these two measurements should result in substantially identical measurements during normal operation of the anesthetic breathing apparatus. In case of deviations, the measurement based on redundant measurement at the same sampling point by the two independent gas analyzers may be performed to identify potential malfunctions.

In some embodiments a ratio of measurable agents or gases may be used for this verification purpose, e.g. a ratio of two anesthetic agents during inspiration (in case provideable by the anesthetic breathing apparatus, e.g. by means of a second anesthetic agent delivery device), a ratio of Oxygen to Nitrous Oxide during inspiration, etc. In case of deviations, the measurement based on redundant measurement at the same sampling point by the two independent gas analyzers may be performed to identify potential malfunctions.

Thus, in some embodiments, the gas measurement data of the first gas analyzer 200 and the gas measurement data of said second gas analyzer 210 may be related to the same specific single anesthetic agent, the same specific single gaseous component, and/or a ratio of specific agents or gases measureable by both the first and second gas analyzers. In addition, or alternatively, upon detection of a first disproportion detected, e.g. based on the same specific single anesthetic agent, a backup comparison may be made for verification purposes, e.g. based on the same specific single gaseous component.

Returning to FIG. 1, the second gas analyzer 210 is thus, in the second mode of operation of switch over unit 240 arranged for patient monitoring, e.g. for providing data for visually showing curves and measured inspiratory and expiratory gas parameters on a screen. Measurement data may be provided to input/output interface 58 with command input means and display means known in the art of anesthetic breathing apparatuses.

The anesthetic breathing apparatus may be operated in a mode of operation comprising alternating the switch over unit 240 between its two modes of operation.

The switch over unit 240 may be controlled by control unit 65, and in normal operation of the anesthetic breathing apparatus, be operated in the second mode of operation, comprising normally sampling at the Y-piece 4. In case a too large deviation of the two measurement values provided to the control unit 65 via lines 67, 68 is detected by the control unit, the sampling point 290, 292 is switched by switch over unit 240 turning to its first mode of operation, i.e. to the internal sampling point 190, 192. In case the two measured gas concentration values, provided by the first gas analyzer 200 and the second gas analyzer 210, no longer substantially differs from each other, this is an indication that at least one of sample lines 232, 234 is occluded, e.g. clogged by mucus conveyed from the patient during exhalation.

In this way an occlusion of the sampling lines 232, 234 connected to the Y-piece close to the patient may be detected and the vaporizer does not need not be switched off since the measurement of anesthetic agent concentration may now be correctly done via an unclogged line, close to the vaporizer. The clogged line may be cleaned or replaced in the meantime, and repeating the above switching procedure by switching unit 240 back to the second mode of operation, may confirm a successful action and unclogged line by a comparison of the measurement values of the two gas analyzers not revealing a substantial difference any longer during an inspiratory phase of said anesthetic breathing apparatus.

If, on the other hand, the switching from the second mode of operation, comprising normally sampling at the Y-piece 4, to the first mode of operation, to the internal sampling point 190, 192, still results in a difference between the two measured gas concentration values, provided by the first gas analyzer 200 and the second gas analyzer 210, this is an indication that another defect is present in the anesthetic breathing apparatus. For instance, one of the first and second gas analyzers 200, 210 may be defective. In this case, suitable action may be taken, including alarming the operator and/or shutting off the anesthetic vaporizer 22.

Hence, the anesthetic breathing apparatus comprises a first gas analyzer arranged to provide gas measurement data related to a first sample point to a control unit that is arranged in a feedback control system configured to adjust delivery of a vaporized anesthetic agent from an anesthetic vaporizer to a delivery point in an inspiratory branch of a breathing circuit of the anesthetic breathing apparatus, wherein the first sampling point is arranged in the breathing circuit downstream and close to the delivery point; a second gas analyzer arranged to be operated in a first mode of operation to provide gas measurement data for patient monitoring, and arranged to be operated in a second mode of operation to provide gas measurement data to the control unit; and wherein the second gas analyzer is arranged to sample at a second sample point arranged close to a patient connection for the first mode of operation and at the first sampling point in the second mode of operation.

The anesthetic breathing apparatus may implement a method of improving monitoring of anesthetic agents in an anesthetic breathing apparatus. The method includes providing gas measurement data related to a first sample point from a first gas analyzer to a control unit, and adjusting delivery of a vaporized anesthetic agent from an anesthetic vaporizer to a delivery point in an inspiratory branch of a breathing circuit of the anesthetic breathing apparatus by the control unit in a feedback control system, wherein the first sampling point is arranged in the breathing circuit downstream and close to the delivery point. The method further includes providing gas measurement data from a second gas analyzer in a first mode of operation for patient monitoring, and in a second mode of operation providing gas measurement data to the control unit. The method includes switching fluid communication of the second gas analyzer between the first sample point for the second mode of operation and a second sample point for the first mode of operation by controlling a switch over unit fluidly connected to the second gas analyzer the first and second sample point, wherein the second sample point is arranged close to a patient connection a patient connected to the breathing circuit.

The method may be implemented as a computer-readable storage medium encoded with programming instructions for processing by a computer for improving monitoring of anesthetic agents in an anesthetic breathing apparatus. The programming instructions include a first code segment for providing gas measurement data related to a first sample point from a first gas analyzer to a control unit, and adjusting delivery of a vaporized anesthetic agent from an anesthetic vaporizer to a delivery point in an inspiratory branch of a breathing circuit of the anesthetic breathing apparatus by the control unit in a servo or feedback control system, wherein the first sampling point is arranged in the breathing circuit downstream and close to the delivery point. The programming instructions include a second code segment for providing gas measurement data from a second gas analyzer in a first mode of operation for patient monitoring, and in a second mode of operation providing gas measurement data to the control unit. The programming instructions include a third code segment for switching fluid communication of the second gas analyzer between the first sample point for the second mode of operation and a second sample point for the first mode of operation by controlling a switch over unit fluidly connected to the second gas analyzer the first and second sample point, wherein the second sample point is arranged in a patient tubing close to a patient connected to the breathing circuit.

In FIG. 2 a schematic drawing is shown illustrating another embodiment of the invention. The main difference to the embodiment described with reference to FIG. 1, is that the anesthetic vaporizer 22 is arranged directly in the breathing circuit without an intermediate fluid connection line. This may be implemented by having an electronically controlled injector vaporizer, which has a vaporizing chamber that is integrated into the tubing of the breathing circuit 7. This embodiment provides an even faster servo feedback and control of anesthetic agent concentration in the breathing circuit 7.

In FIG. 3 an exemplary anesthetic breathing apparatus is illustrated comprising an embodiment of the invention. However, embodiments of the invention may also be implemented in various other breathing apparatuses, such as those disclosed in WO2007/071756 of the same applicant as the present application, which is incorporated by reference in its entirety, an in particular with reference to the apparatuses described in FIGS. 1 and 7 thereof, for all purposes.

Now turning to the present embodiment with reference to FIG. 3, a servo or feedback control system comprising a first gas analyzer 200 continuously during the inspiration regulates the amount of rebreathing of gas exhaled from the patient and stored during expiration in a volume reflector, versus the amount of fresh gas (oxygen and anesthesia-gases). The servo or feedback control system decreases the amount of fresh gas to a suitable low value that still is enough for keeping the gas concentrations at set values.

In more detail, in FIG. 3 a breathing circuit of an anesthetic breathing apparatus is shown schematically, coupled to a circle system 7 with a mechanical ventilation system 53.

The airways of the patient 1 are connected to the patient tube 2 of the Y-piece 4 in a circular tubing system with the inspiration tube 6 provided with a first one-way valve 8 and the expiration tube 10 provided with a second one-way expiratory valve 12. A patient pressure sensor 74 is provided in the patient tube 2 connected to the Y-piece 4. Downstream the second one-way valve 12, in FIG. 3 in a clockwise direction along the circle system 7, a common expiration and inspiration line 14 is provided for the delivery of inspiration gas to the patient and evacuation of expiration gas from the patient. The common expiration and inspiration line 14 is coupled to the circle system 7 at a junction 15. Further along the circle system 7, the tubing passes through a $CO_2$ absorber 16.

Downstream the $CO_2$ absorber 16 a gas supply branch line 18 is provided to feed gas into the circle system 7 from a gas source. The gas supply branch line 18 is coupled to the circle system 7 at a junction 19, wherein the anesthetic vaporizer 22 may provide a desired amount of an anesthetic agent, as set by control line 69.

The common expiration and inspiration line 14 may be provided with a volume reflector and/or adsorption filter 26 devised for adsorption and desorption of anesthetic and respiration gases to or from the patient.

The fresh gas inhalation source may comprise multiple gas sources, such as an oxygen gas source 20A, and an air gas source 20B, as illustrated in FIG. 3. Additionally, the fresh inhalation gas source may comprise a nitrous oxide gas source 20C, such as shown in FIG. 3, selectable instead of the air gas source by selection valve 80.

The anesthetic vaporizer 22 is fluidly connected to the fresh gas supply branch line 18 downstream the multiple gas sources and upstream the junction 19. The anesthetic vaporizer 22 is devised for vaporizing a liquid volatile anesthetic agents in the fresh gas flow that is delivered into the circle system 7 and with a flow of inspiratory gas to the patient 1. In an exemplifying breathing circuit the vaporizer 22 may be an injection type vaporizer.

The first gas analyzer 200 and the second gas analyzer 210 are provided to analyze gas contents with an input of sample inspiratory gas in a sidestream. The sidestream is tapped downstream the junction 19 and upstream a first one-way valve 8 in the inspiratory branch. After analysis in the first gas analyzer 200 the sample gas is recirculated to the inspiratory flow downstream the first one-way valve 8 and upstream the Y-piece 4 in the inspiratory branch 6. The same applies to the second gas analyzer 210, depending on the mode of operation of the switching unit 240.

As elucidated above, the first gas analyzer 200 provides gas measurement data via a line 67 to the control unit 65, which in this embodiment is connected to an anesthetic agent control unit 64. The second gas analyzer 210 provides gas measurement data via a line 68 to the control unit 65. The control unit 65 is part of a servo or feedback control system, using the gas measurement data from the first gas analyzer provided via line 67 as a feedback signal via the anesthetic agent control unit 64 and control line 69 for adjusting delivery of a vaporized anesthetic agent from the anesthetic vaporizer 22. In the present embodiment, the vaporizer 22 is positioned outside of a patient breathing circle 7 of the anesthetic breathing apparatus.

A pressure sensor 70 is provided between the first one-way valve 8 and the recirculation point of the sample gas.

At the side turned opposite the circle system 7, the adsorption filter or volume reflector 26 of the common expiration and inspiration line 14 is coupled at a junction 24 to a first output branch line 51 from a fourth inspiratory valve 35 supplied with gas from a gas source 20D.

Oxygen gas source 20A is coupled to an $O_2$ inspiratory valve 30 that in its turn is connected to a blender 34. Similarly, air gas source 20B or nitrous oxide gas source 20C is coupled to a second inspiratory valve 32 that also is coupled to the blender 34. The $O_2$ inspiratory valve 30 and the second inspiratory valve 32 are devised for adjusting the inlet flow and the proportions of the respective gases into the blender 34 and further into fresh gas line 18.

An evacuation line 36 is connected to the common expiration and inspiration line 14 and to the mentioned first output branch line 51 at the junction 24. The evacuation line 36 leads via a flow meter 38 and a pressure sensor 76 to an expiratory valve 40 that is devised to control output of evacuated gas flow from the circle system 7 to a scavenging system 42 or to the atmosphere.

The mechanical ventilation system 53 and the expiratory valve 40 as well as other components may be parts of a per se known mechanical ventilator with a ventilation control system 56. The ventilation control system 56 may have a user input/output interface 58 with command input means and display means of a known type.

Also in a per se known manner, the ventilation control system 56 may comprise mechanical ventilation control unit 60 usually embodying specifically designed computer program code for controlling the operation of the mechanical ventilation system 53 and its components via a symbolically shown control line 62.

The ventilation control system 56 further has an anesthetic agent control unit 64. The anesthetic agent control unit 64 is devised to control the anesthetic vaporizer 22 via the symbolically shown control line 69.

As described above, the switch over unit 240 comprises one or more on-off valves suitably arranged for either coupling the first set of lines 222, 224 or the second set of lines 232, 234 to the third set of lines 212, 214 with the second gas analyzer 210.

The anesthetic breathing apparatus may thus be operated in the above described mode of operation comprising alternating the switch over unit 240 between its two modes of operation, i.e. for redundant measurements of anesthetic gases, or for patient monitoring by means of the second gas analyzer 210.

An automatic detection that the sampling point to which the second gas analyzer is fluidly connected is the second sampling point 290 may be done by analyzing the $CO_2$ content of the gases measured by the second gas analyzer 210. In case the patient connection 2 is connected to the Y-piece 4 and the breathing circuit 7, the patient's alveolar gas will cause a variation of $CO_2$ content a the second sampling point 290 between inspiration (lower $CO_2$ measurement values) and expiration (higher $CO_2$ measurement values).

For instance in a capnographic measurement different phases of inspiration and expiration may be identified from the curvature of the $CO_2$ measurement over time. During expiration the $CO_2$ content increases. When such a variation of $CO_2$ concentration is measured, this means that the second gas analyzer 210 is connected to the sampling point at the Y-piece 4, both detecting inspiration and expiration phases.

This automatic detection may advantageously be used by the control unit 65 in order to identify the status of the second sampling point 290 currently being in connection to the second gas analyzer 210. In some embodiments this is equivalent to the switching status of the switch over unit 240 being in the in the second mode of operation thereof, arranged for patient monitoring. In absence of a $CO_2$ variation, this may be an indication that the patient connection 2 is not to the patient, that the sample line 232 is not connected to the sample point 290, or that the second gas analyzer is fluidly connected to the first sampling point 190. This may be verified by analyzing the present values of Oxygen and/or Nitrous Oxide measured by the second gas analyzer 210, i.e. an $O_2$ concentration corresponding to ambient air may be detected, or a Nitrous Oxide concentration detected may be an indication that a connection to the breathing circuit is provided.

In this manner patient safety and operational safety of the anesthetic breathing apparatus may be increased as it may be secured that the second gas analyzer, i.e. the sampling tube 232, is correctly connected to the anesthetic breathing apparatus and/or that a patient is correctly connected to the patient tube 2.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

We claim as our invention:

1. A method of monitoring anesthetic agents in an anesthetic breathing apparatus, wherein said anesthetic breathing apparatus comprises a control unit, a breathing circuit in fluidic connection with an anesthetic agent delivery device, a first gas analyzer, and a second gas analyzer, said method comprising:
providing first gas measurement data for gas sampled from a first sample point from said first gas analyzer to a said control unit, wherein said first sampling point is arranged in an inspiratory branch of said breathing circuit downstream from and in proximity of an anesthetic agent delivery point;
adjusting delivery of a vaporized anesthetic agent from said anesthetic agent delivery device to said anesthetic agent delivery point in an inspiratory branch of said breathing circuit by said control unit in a feedback control system,
providing second gas measurement data from a second gas analyzer in a first mode of operation and in a second mode of operation; and
switching said second gas analyzer between said first and second modes of operation; wherein:
said switching between said first and second modes of operation comprises switching fluid communication of said second gas analyzer between said first sample point for said second mode of operation and a second sample point arranged in a patient tubing close to a Y-piece at a patient connected to said breathing circuit for said first mode of operation and
said switching between said first and second modes of operation comprises controlling a switch over unit fluidly connecting said second gas analyzer to said first and second sample points.

2. The method according to claim 1, further comprising redundantly measuring gas concentrations in the breathing circuit at the first sample point with said first and second gas analyzers.

3. The method according to claim 2, further comprising comparing measured gas concentration data provided by said first and second gas analyzers in said first mode of operation during an inspiratory phase of said anesthetic breathing apparatus.

4. The method according to claim 3, further comprising initiating one or more of a an alarm, a shutdown of said anesthetic agent delivery device, and switching said second gas analyzer to said second mode of operation when said comparison results a difference of measured gas concentrations that exceeds a specified difference threshold value.

5. The method according to claim 4, wherein switching said second gas analyzer to said second mode of operation is initiated and said method further comprises providing an indication that a line connected from said switching apparatus to said second sample point is occluded when said comparison in said second mode of operation results in no substantial difference of said measured gas concentration data provided by the first and second gas analyzers.

6. The method according to claim 4, wherein switching said second gas analyzer to said second mode of operation is initiated and said method further comprises providing an indication that a defect is present in the anesthetic breathing apparatus when said comparison in said second mode of operation results in no substantial difference of said measured gas concentration data provided by the first and second gas analyzers.

7. The method according to claim 1, further comprising positioning said anesthetic agent delivery device outside of said patient breathing circuit.

8. The method according to claim 1, further comprising arranging said anesthetic agent delivery device in the breathing circuit without an intermediate fluid connection line.

9. The method according to claim 1, further comprising determining whether said second gas analyzer is fluidly connected to said second sample point based on a variation of $CO_2$ concentration measured by said second gas analyzer.

10. The method according to claim 1, wherein said gas measurement data of said first and second gas analyzers are related to the same specific single anesthetic agent, the same specific single gaseous component, and/or a ratio of specific agents or gases measureable by both said first and second gas analyzers.

11. An anesthetic breathing apparatus comprising:
a breathing circuit comprising an inspiratory branch and a Y-piece comprising tubing adapted for connection to a patient, said breathing circuit being configured to receive an anesthetic agent from an anesthetic delivery device and to deliver vaporized anesthetic agent at a delivery point in said inspiratory branch;
a feedback control system comprising a control unit configured to automatically adjust delivery of said vaporized anesthetic agent at said delivery point;
a first gas analyzer configured to provide gas measurement data obtained from a first sample point to said control unit, said first sample point being located in said breathing circuit downstream from and in close proximity to said delivery point;
a second gas analyzer configured for operation in a first mode to provide gas measurement data for patient monitoring, and in a second mode to provide gas measurement data to said control unit; wherein
said second gas analyzer is configured to obtain gas measurement data for a second sample point in said tubing in close proximity to said Y-piece in said first mode of operation and to sample gas measurement data at said first sample point in said second mode; and
a switchover unit in fluid connection with said second gas analyzer, and configured to switch fluid communication of said second gas analyzer between said first sample point and said second sample point.

12. The apparatus according to claim 11, wherein said second gas analyzer is configured in said second mode of operation to redundantly measure gas concentration in the breathing circuit at said first sample point.

13. The apparatus according to claim 11, wherein said control unit is configured to compare measured gas concentrations provided by said first gas analyzer and said second gas analyzer in said first mode, during an inspiratory phase of said breathing circuit.

14. The apparatus according to claim 13, wherein said control unit is configured to emit an alarm, discontinue operation of said anesthetic agent delivery device, or switch said second gas analyzer to operate in said second mode when a difference in gas concentrations provided by said first and second gas analyzers exceeds a predetermined value.

15. The apparatus according to claim 14, wherein said control unit is configured to switch said second gas analyzer to said second mode of operation and to cause emission of a humanly perceptible indication that a line connected from said second gas analyzer to said second sample point is occluded when there is no substantial difference between gas concentrations measured at the first sample point by said first and second gas analyzers.

16. The apparatus according to claim 14, wherein said control unit is configured to switch said second gas analyzer to said second mode of operation and to cause emission of a humanly perceptible indication that a fault is present in said anesthetic breathing apparatus when there is no substantial difference between gas concentrations measured at the first sample point by said first and second gas analyzers.

17. The apparatus according to claim 11, wherein said control unit is configured to determine when said second gas analyzer is in fluid communication with said second sample point by evaluating a variation of $CO_2$ concentration measured by said second gas analyzer.

18. The apparatus according to claim 11, wherein said first and second gas analyzers generate gas measurement data selected from the group consisting of gas measurement data for a same, single anesthetic agent, gas measurement data for a same, single gas component, a ratio of two different anesthetic agents, and a ratio of two different gas components.

19. The apparatus according to claim 11, wherein said anesthetic agent delivery device is located outside of said breathing circuit.

20. The apparatus according to claim 11, wherein said anesthetic agent delivery device is located in said breathing circuit, without an intermediate fluid connection line therebetween.

21. The apparatus according to claim 11, wherein said anesthetic agent delivery device is an anesthetic vaporizer.

22. The apparatus according to claim 11, wherein said anesthetic agent delivery device is configured to deliver a dose of a gaseous anesthetic agent into said breathing circuit.

23. A non-transitory computer-readable storage medium encoded with programming instructions, said storage medium being loaded into a control unit of an anesthetic breathing apparatus, and said programming instructions causing said control unit to:
receive gas measurement data related to a first sample point from a first gas analyzer, and adjust delivery of a vaporized anesthetic agent from an anesthetic agent delivery device to a delivery point in an inspiratory branch of a breathing circuit of said anesthetic breathing apparatus in a feedback control system, wherein said first sampling point is arranged in said breathing circuit downstream and close to said delivery point;
receive gas measurement data from a second gas analyzer in a first mode of operation for patient monitoring, and in a second mode of operation to provide gas measurement data to said control unit; and
switch fluid communication of said second gas analyzer between said first sample point for said second mode of operation and a second sample point for said first mode of operation by controlling a switch over unit fluidly connected to said second gas analyzer said first and second sample point, wherein said second sample point is arranged in a patient tubing close to a Y-piece at a patient connected to said breathing circuit.

* * * * *